Jan. 9, 1973 B. C. COWARD Plant Pat. 3,288
CHRYSANTHEMUM PLANT
Filed Feb. 26, 1971
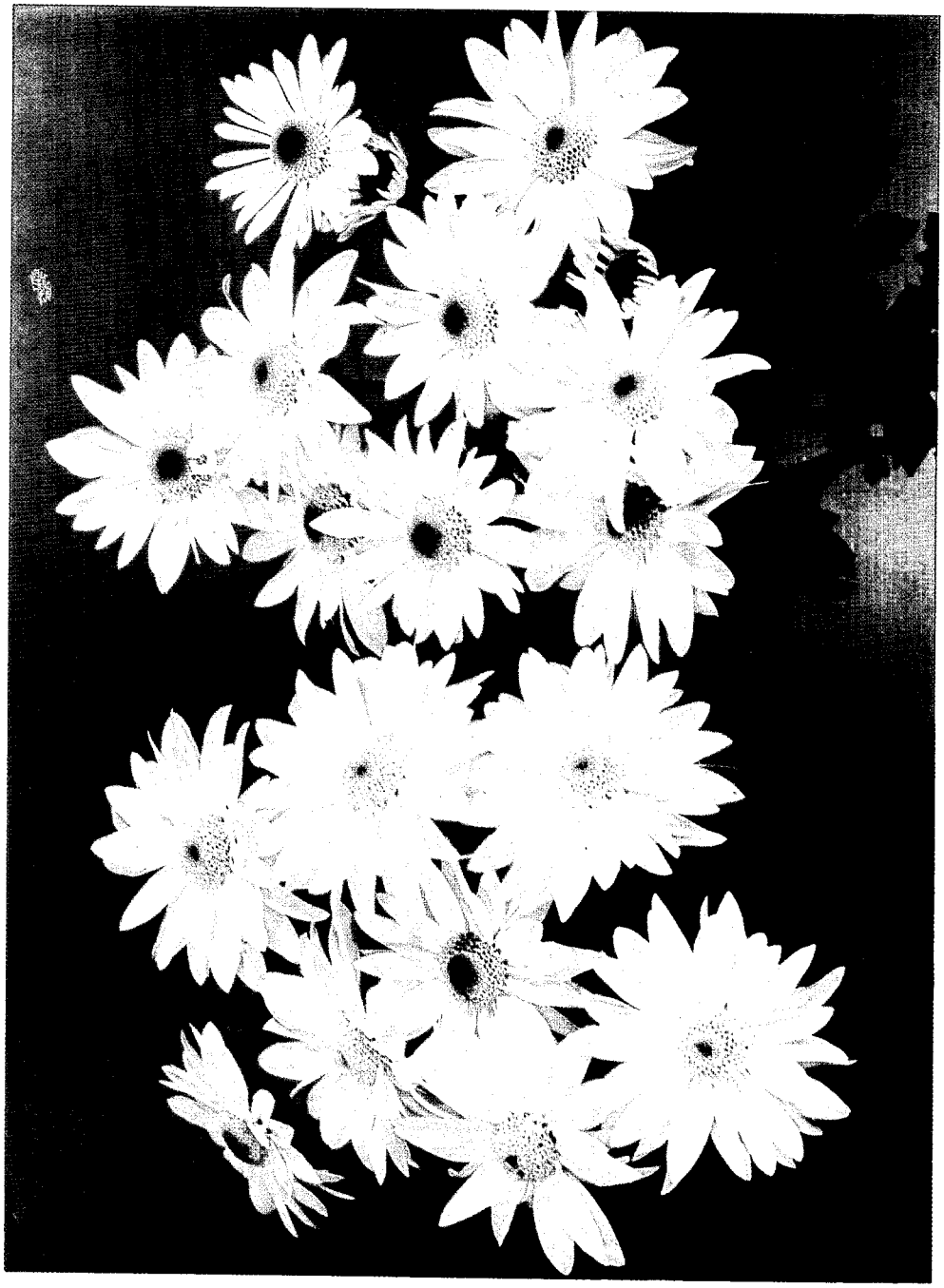

United States Patent Office

Plant Pat. 3,288

Patented Jan. 9, 1973

3,288

CHRYSANTHEMUM PLANT

Bob G. Coward, Fort Myers, Fla., assignor to Yoder Brothers, Inc., Barberton, Ohio

Filed Feb. 26, 1971, Ser. No. 119,422

Int. Cl. A01h *5/00*

U.S. Cl. Plt.—74 1 Claim

The present invention comprises a new and distinct cultivar of chrysanthemum plant which is a sport of the unpatented cultivar known commercially in the United States as Bronze Marble.

The new cultivar is similar in many respects to the cultivar Yellow Marble, also an unpatented but well-known commercial cultivar, and the cultivar Gold Marble, disclosed and claimed in pending application Ser. No. 80,257, filed Oct. 14, 1970, of Walter H. Jessel, Jr. and William E. Duffett. The new cultivar has the same characteristics as Yellow Marble and Gold Marble of:

(1) Nine week response.
(2) A similar recommended flowering period.
(3) Daisy flower form.
(4) Foliage color and shape.

The new cultivar is distinguished from Yellow Marble by the following characteristics, when grown under comparable conditions:

(1) Flowers approximately one-quarter (¼) inch larger.
(2) Darker yellow color with less oxidization of color as flowers mature.
(3) Fewer green bracts in center of flower in high temperature periods.
(4) Approximately 2" more vigor.

and is distinguished from Gold Marble by the following characteristics, when grown under comparable conditions:

(1) Approximately eight to ten inches more vigor, thus being comparable, in terms of vigor, to the rest of the well-known Marble family.
(2) A lighter flower color.
(3) Flowers approximately one-half to three-quarters of an inch larger.
(4) Approximately three to four fewer flowers per stem.
(5) A more vegetative or less reproductive selection which produces a more terminal, less compound spray formation.
(6) Approximately 2–3 days later in response to Spring, and 2–3 days earlier response in Fall.

The new cultivar was asexually reproduced by cuttings at Fort Myers, Fla., and has been found during stabilization to retain its distinctive characteristics through successive propagations.

The new cultivar when grown in the vicinity of Barberton, Ohio has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States, and coastal California is from May through October, and Florida, December through April.

The accompanying drawing is a comparison photograph of the new cultivar, which appears on the left, and Yellow Marble, which appears on the right.

In the description which follows, color references are to the Munsell Color Book, 1963 edition, and comparisons are made with the cultivar Yellow Marble and Gold Marble. Where only the value or description of the new cultivar appears, such value or description applies also to the comparison cultivars.

Botanical Classification: *Chrysanthemum morifolium*

| | Florida Marble | Yellow Marble | Gold Marble |
|---|---|---|---|
| Bloom: | | | |
| Size | 2¾" | 2½" | 2". |
| Fully expanded | 3¼" | 3" | 2¾". |
| Borne | In compound lateral clusters of 5–8 flowers. | In compound lateral clusters of 5–8 flowers. | In compound lateral clusters of 8–12 flowers per lateral. |
| Stems | Wiry | | |
| Form | Daisy | | |
| Permanence | 7 days | | |
| Color: | | | |
| Center of flower | Light green, 2.5GY5/8 to dark yellow, 6.25Y8.5/12 | | |
| Base of petals | Yellow, 7.5Y8.5/10 | Light yellow, 7.5Y9/6 | Dark yellow, 6.25Y8.5/12. |
| Inside of petals | Yellow, 7.5Y8.5/10 to light yellow, 7.5Y9/6. | Light yellow, 7.5Y9/6 to pale yellow, 7.5Y9/4. | Dark yellow, 6.25Y8.5/12. |
| Reverse of petals | Yellow, 7.5Y8.5/8 to light yellow, 7.5Y9/6. | Pale yellow, 7.5Y9/4 | Yellow, 7.5Y8.5/10. |
| Tonality from a distance | Yellow | Light yellow | Golden yellow. |
| Discoloration | Light yellow | Pale yellow | None. |
| Petals: | | | |
| Texture | Smooth | | |
| Appearance and form | Open at base, broad at mid-point, tapering to a rounded point | | |
| Arrangement | Composite, whorled on a single receptacle | | |
| Persistence | Resist shatter | | |
| Fragrance | Typical chrysanthemum | | |
| Stamen, anthers | 250–250 | | |
| Pollen | None to abundant (functional sterility) | | |
| Arrangement | Clustered in center of flower, if present | | |
| Styles | Present in both ray and disc florets | | |
| Length | Short | | |
| Ovaries | At the base of petal attached to receptacle | | |
| Plant: | | | |
| Form | Herbaceous | | |
| Growth | Upright | | |
| Height | Approximately 44"–49" on single stem crops given 2 to 4 long day weeks and a total crop time of 12–13 weeks, depending on the season as defined in the timetables published by Yoder Bros., Inc. | Approximately 42"–47" on single stem crops given 2 to 4 long day weeks and a total crop time of 12–13 weeks, depending on the season as defined in the timetables published by Yoder Bros., Inc. | Approximately 36"–39" on single stem crops given 2 to 4 long day weeks and a total crop time of 12–13 weeks, depending on the season as defined in the timetables published by Yoder Bros., Inc. |
| Spread | None when grown single stem to moderate when pinched | | |
| Foliage: | | | |
| Top side | Dark green, 7.5GY3/4 | | |
| Size | 6" long, 3 3/16" wide | 5¾" long, 3¼" wide | 5¾" long, 3¼" wide. |
| Quantity | | Numerous | |
| Shape | | Spatulate lobed | |
| Texture | | Smooth | |
| Ribs and veins | | Prominent | |
| Edge | | Moderately indented | |
| Serration | | Moderate | |
| Under side | | Light green, 7.5GY5/4 | |
| Stipules | | Prominent | |

I claim:

1. A new and distinct cultivar of chrysanthemum characterized particularly as to its uniqueness when compared to the parent cultivar Yellow Marble by its approximately one-quarter inch larger flowers, darker yellow flower color with less oxidation of color as flowers mature, fewer green bracts in center of flower in high temperature periods, and approximately two inch more vigor, and characterized as to uniqueness when compared to the cultivar Gold Marble by its flowers which are lighter yellow in color and approximately one-half to three-quarters of an inch larger, approximately eight to ten inches more vigor and three to four fewer flowers per stem, its more vegetative or less reproductive selection which produces a more terminal, less compound spray formation, and its approximately 2–3 later response in spring and 2–3 days earlier response in fall.

No references cited.

ROBERT E. BAGWILL, Primary Examiner